United States Patent [19]

Zaiger

[11] Plant 4,571

[45] Jul. 15, 1980

[54] PEACH TREE

[76] Inventor: Chris F. Zaiger, 537 Rosemore Ave., Modesto, Calif. 95351

[21] Appl. No.: 5,578

[22] Filed: Jan. 22, 1979

[51] Int. Cl.[3] ..... A01H 5/00
[52] U.S. Cl. ..... Plt./43
[58] Field of Search ..... Plt./43

*Primary Examiner*—Robert E. Bagwill

*Assistant Examiner*—James R. Feyrer

[57] ABSTRACT

A variety of peach tree which is medium to large size, vigorous, medium dense and upright in growth; the tree being a regular and productive bearer of large size, firm, yellow flesh, freestone fruit with yellow skin substantially overspread with red; the fruit is further characterized by excellent eating quality and ability to ship to long distance markets.

4 Drawing Figures

ORIGIN OF THE VARIETY

The new variety of peach tree was originated by me in my experimental orchard near Modesto, Calif. as a second generation seedling of a cross between O'Henry Peach, (U.S. Plant Pat. No. 2,964) and Giant Babcock Peach, (U.S. Plant. Pat. No. 1,353).

ASEXUAL REPRODUCTION OF THE VARIETY

The present variety of peach tree was asexually reproduced by grafting and budding at my experimental orchard, located at Modesto, Calif. and shows that such reproductions run true to the original tree in all respects.

SUMMARY OF THE VARIETY

The present variety of peach tree is of medium to large size, vigorous, upright growth and a productive and regular bearer of large, firm, yellow flesh, freestone fruit with yellow skin substantially overspread with red. The fruit characterized by ripening and harvesting approximately two weeks before O'Henry Peach, (U.S. Plant Pat. No. 2,946) and having excellent eating and shipping quality.

PHOTOGRAPHS OF VARIETY

The accompanying photographs show typical specimens of the foliage and fruit of my new variety, with upper and lower surfaces of the foliage being illustrated and a fruit divided on its suture plane to reveal flesh coloration and showing a stone remaining in place. The photographs were taken shortly after being picked at maturity (shipping ripe) and the colors are as nearly true as reasonably possible in a color representation of this type.

DESCRIPTION OF THE VARIETY

This following is a detailed description of the new and distinct variety of peach tree and its foliage and fruit based upon observations of specimens grown near Modesto, Calif., with color terminology in accordance with Reinhold Color Atlas by A. Korneruf and J. H. Wanscher.

Tree:
- *Size.*—Medium to large.
- *Vigor.*—Vigorous.
- *Form.*—Upright.

- *Production.*—Productive.
- *Density.*—Medium dense.
- *Bearing.*—Regular.

Trunk:
- *Size.*—Medium stocky.
- *Surface.*—Shaggy.

Branches:
- *Size.*—Medium stocky.
- *Lenticels.*—Medium size. Medium number.
- *Texture.*—Smooth to medium rough.

Leaves:
- *Size.*—Large. Average length — 7¾". Average width — 1¾".
- *Form.*—Lanceolate. Acutely pointed.
- *Color.*—Upper surface — (27-F-6 to 28-F-8). Lower surface — (27-E-5 to 28-E-6).
- *Margin.*—Crenate.
- *Texture.*—Smooth.
- *Petiole.*—Medium length. Medium thickness.
- *Glands.*—Average number — 4. Large — reniform. Positioned on lower part of leaf blade and upper part of petiole.

Flower buds:
- *Size.*—Medium.
- *Length.*—Medium.

Flowers:
- *Blooming period.*—First bloom — Mar. 3, 1976. Full bloom — Mar. 10, 1976.
- *Size.*—Large — showy. Color — pink.

Fruit:
- *Maturity when described.*—Hard ripe.
- *Date of first picking.*—July 29, 1976. Aug. 5, 1976.
- *Size.*—Comparatively uniform. Large. Average diameter axially — 2¾" to 3". Average transversely in suture plane — 2⅝" to 3".
- *Form.*—Globose.
- *Suture.*—Usually shallow, extends from base to apex.
- *Ventral surface.*—Usually rounded, varies from equal to unequal.
- *Cavity.*—Moderately rounded, only slightly elongated in suture plane. Average depth — ½". Average breadth — 1".
- *Base.*—Retuse.
- *Apex.*—Rounded to slightly retuse.

Skin:
- *Thickness.*—Medium.
- *Texture.*—Medium tender.

*Tendency to crack.*—None.
*Down.*—Moderate. Medium length.
*Color.*—Bright yellow ground color — (4-A-8 to 5-A-7) overspread with red — (8-A-8) — (9-B-8).

Flesh:
*Amygdalin.*—Undetected.
*Juice.*—Moderate.
*Texture.*—Firm.
*Fibers.*—Few — tender.
*Ripens.*—Uniform.
*Flavor.*—Mild.
*Aroma.*—Fragrant.
*Eating quality.*—Excellent.
*Color.*—Dark yellow (4-A-8) to cadmium orange (5-A-8).

Stone:
*Type.*—Free.
*Size.*—Medium to large. Average length — 1½". Average width — 1 1/16". Average thickness — ⅝". Surface of pit cavity red (10-B-7) with yellow fibers.
*Form.*—Ovoid.
*Base.*—Straight to slightly oblique.
*Apex.*—Acuminate.

*Side.*—Equal.
*Surface.*—Irregularly furrowed toward apex, pitted toward base.
*Ridges.*—Rounded toward apex.
*Tendency to split.*—Slight.
*Color.*—Light tan (8-C-5).

Use: Market. Dessert.
Keeping quality: Very good.
Shipping quality: Excellent.

The tree and its fruit herein described may vary in slight detail due to climatic and soil conditions under which it may be grown; the description is that of the variety produced under ecological conditions at Modesto, Calif.

The following is claimed:

1. A new and distinct variety of peach tree, as illustrated and described, characterized by its regular and productive bearing of large size, yellow flesh, firm, freestone fruit, with excellent eating and shipping quality and is further characterized — by having attractive red skin color, uniform ripening and maturing two weeks before O'Henry Peach (U.S. Plant. Pat. No. 2,964).

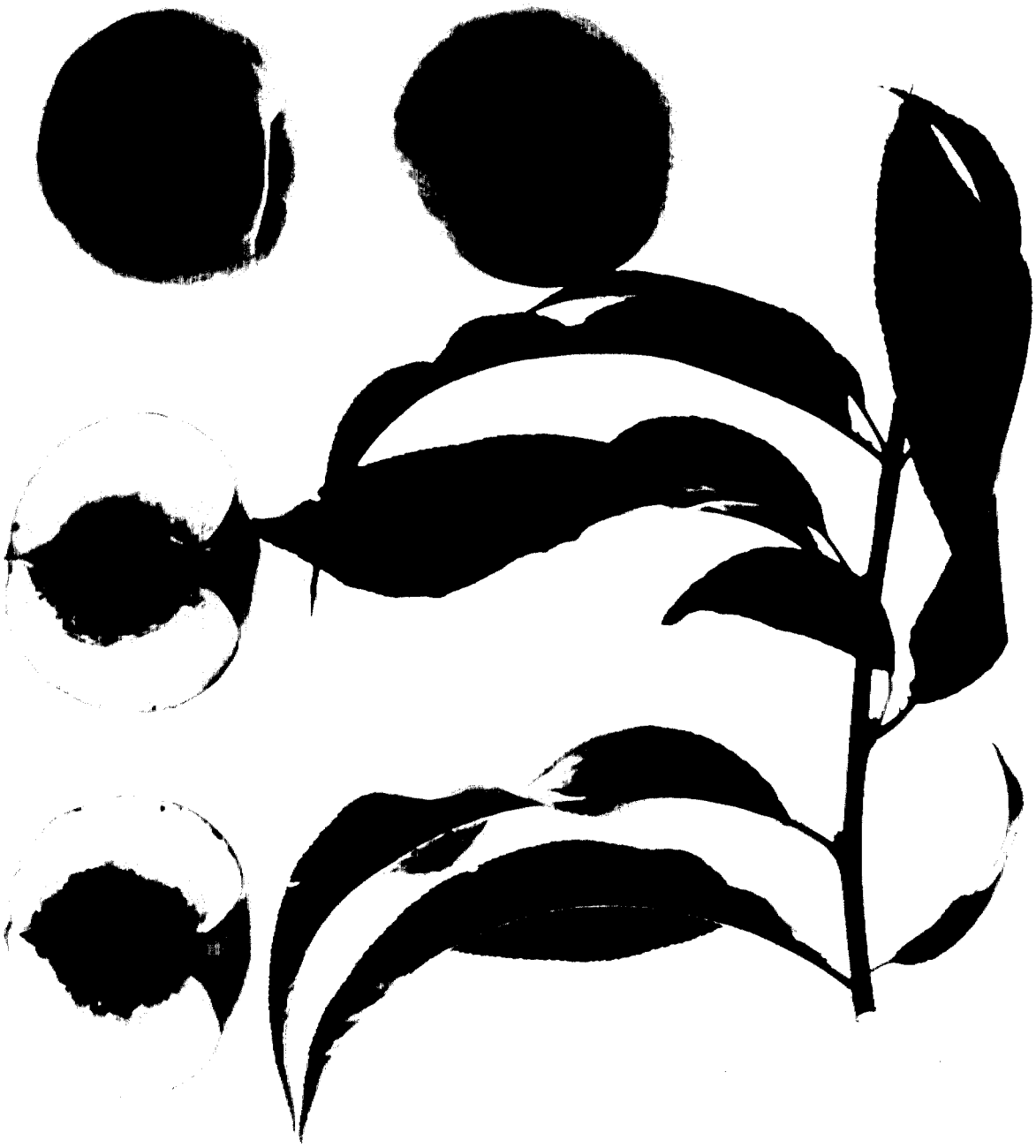

* * * * *